US011263775B2

(12) United States Patent
Davies et al.

(10) Patent No.: US 11,263,775 B2
(45) Date of Patent: Mar. 1, 2022

(54) SYSTEM FOR AND METHOD OF SURVEYING A SURFACE

(71) Applicant: SOLETANCHE FREYSSINET S.A.S., Rueil-Malmaison (FR)

(72) Inventors: Michael Davies, Newbury (GB); Gary Bethel, Abingdon (GB); Robert Clark, Thatcham (GB); Dominique Rothan, Aigremont (FR)

(73) Assignee: SOLETANCHE FREYSSINET S.A.S., Rueil-Malmaison (FR)

( * ) Notice: Subject to any disclaimer, the term of this patent is extended or adjusted under 35 U.S.C. 154(b) by 0 days.

(21) Appl. No.: 16/967,263

(22) PCT Filed: Feb. 8, 2019

(86) PCT No.: PCT/EP2019/053203
§ 371 (c)(1),
(2) Date: Aug. 4, 2020

(87) PCT Pub. No.: WO2019/155024
PCT Pub. Date: Aug. 15, 2019

(65) Prior Publication Data
US 2020/0357133 A1    Nov. 12, 2020

(30) Foreign Application Priority Data
Feb. 9, 2018    (GB) ...................... 1802113

(51) Int. Cl.
*G01B 11/22*    (2006.01)
*G01T 1/169*    (2006.01)
(Continued)

(52) U.S. Cl.
CPC ............... *G06T 7/73* (2017.01); *G01B 11/22* (2013.01); *G01T 1/169* (2013.01);
(Continued)

(58) Field of Classification Search
None
See application file for complete search history.

(56) References Cited

U.S. PATENT DOCUMENTS

| 6,135,955 A | 10/2000 | Madden et al. |
| 9,563,955 B1 | 2/2017 | Kamarshi et al. |

(Continued)

FOREIGN PATENT DOCUMENTS

| CN | 101377547 A | 3/2009 |
| EP | 3086283 A1 | 10/2016 |

(Continued)

OTHER PUBLICATIONS

International Search Report (Form PCT/ISA/210) for International Application No. PCT/EP2019/053203 dated May 23, 2019, 3 pages.
(Continued)

*Primary Examiner* — Patricia I Young
(74) *Attorney, Agent, or Firm* — Withrow & Terranova, P.L.L.C.; Vincent K. Gustafson

(57) ABSTRACT

A system for surveying a surface (2) to measure a physical or chemical property associated with the surface. The system includes a handheld probe (4) measuring a physical or chemical property at locations over a surface (2). The video camera (12) captures video data of a user (6) using the handheld probe (4) to survey the surface. The depth sensing device (14) measures the distance to the handheld probe (4). Processing circuitry identifies the handheld probe from the video data and determines the position of the handheld probe (4) relative to the surface (2). A data recorder and/or a data transmitter records and/or transmits data representative of the physical or chemical property measured by the handheld probe (4) and data representative of the associated position (Continued)

of the handheld probe, when the handheld probe (4) is determined to be less than a threshold distance from the surface (2) being surveyed.

19 Claims, 5 Drawing Sheets

(51) Int. Cl.
    *G06T 1/00*     (2006.01)
    *G06T 7/70*     (2017.01)
    *G06T 7/73*     (2017.01)
    *H04N 7/18*     (2006.01)
    *G06K 9/00*     (2022.01)
    *A61B 5/00*     (2006.01)

(52) U.S. Cl.
    CPC ..... *G06K 9/00362* (2013.01); *G06K 9/00718* (2013.01); *H04N 7/18* (2013.01); *A61B 5/0077* (2013.01); *G06T 2207/10016* (2013.01); *G06T 2207/30196* (2013.01); *G06T 2207/30204* (2013.01)

(56) References Cited

U.S. PATENT DOCUMENTS

| | | |
|---|---|---|
| 2004/0075058 A1 | 4/2004 | Blevis et al. |
| 2008/0073495 A1 | 3/2008 | Heckendorn et al. |
| 2008/0048123 A1 | 12/2008 | Larsson et al. |
| 2012/0319950 A1* | 12/2012 | Marks ................. G06F 3/04842 345/158 |
| 2017/0365068 A1 | 12/2017 | Tan et al. |

FOREIGN PATENT DOCUMENTS

| | | |
|---|---|---|
| EP | 3093685 A1 | 11/2016 |
| GB | 2142500 A | 1/1985 |
| GB | 2424704 A | 10/2006 |
| JP | H01296183 A | 11/1989 |
| JP | 2008304350 A | 12/2008 |
| JP | 2017211347 A | 11/2017 |
| WO | 2008002659 A2 | 1/2008 |
| WO | 2013055611 A1 | 4/2013 |
| WO | 2016003863 A2 | 1/2016 |

OTHER PUBLICATIONS

Written Opinion (Form PCT/ISA/237) for International Application No. PCT/EP2019/053203 dated May 23, 2019, 9 pages.
Search Report under Section 17(5) for United Kingdom Patent Application No. GB1802113.9 dated Aug. 1, 2018, 4 pages.
identiFINDER®2, The Next Generation Handheld Radionuclide Identification Device. Datasheet [online], FLIR/Southern Scientific, 2011 [retrieved on Aug. 4, 2020], Retrieved from the Internet: <URL: www.southernscientific.co.uk/data/file/c/3/identiFINDER2_SSL.1438855698.pdf >, 2 pages.

* cited by examiner

SYSTEM FOR AND METHOD OF SURVEYING A SURFACE

This invention relates to a system for and a method of surveying a surface to measure a physical or chemical property associated with the surface. It relates in particular to a system for and a method of surveying a surface to detect the concentration and location of contaminants, e.g. radioactive materials, on the surface in (or having been in) a contaminated (e.g. enclosed) environment.

The monitoring of surfaces in buildings, e.g. for contamination, is a frequent task in health physics and remediation scenarios, notably nuclear facilities. In particular, the presence of small areas of contaminating (e.g. radioactive) materials can result in complications with the demolition of a building and the disposal of the resulting waste. Mapping contamination on such surfaces therefore allows areas of contamination to be identified to allow the contaminating materials to be disposed of correctly.

The process of mapping surface contamination may be performed by marking grids on the surfaces and recording the radiation measurement taken in each grid location manually. However, this process is expensive, time consuming and subject to various problems such as transcription errors, so does not provide the required level of detail easily. Methods of reducing complexity and eliminating errors in the process of mapping surface contamination are sought.

However, the process of collecting measurements of a contaminant using a measurement instrument is one that is difficult to automate. This is owing to the need to move such a measurement instrument close to the surface being mapped in order to be able to detect many of the contaminating materials (e.g. radioactive materials) of the contaminant desired to be measured, and owing to it being difficult to replicate a person's flexibility and dexterity for the variability of surfaces and objects to be surveyed. Thus contamination surveys often require a human surveyor to hold and manipulate the measurement instrument.

Monitors for such contaminating materials, e.g. Geiger counters for radioactive materials, enable the concentration of a particular contaminant to be determined at a particular location. A variety of instruments may be required, depending on the contaminant to be measured. In order to be able to survey a surface (e.g. of a building) properly, the concentration of the contaminating materials needs to be mapped to each of the locations at which the measurements were taken.

However, it is difficult to provide the required position measurements for surveys performed inside buildings or other enclosed environments. These locations are limited by the lack of, or limited, access to facilities such as Global Navigation Satellite Systems (GNSS). Other positioning systems such as robotic total stations (automatic theodolites), ultrasonic or laser ranging systems, and radio-based systems may be used for surveys of enclosed environments. However, the expensive and bulky infrastructure required for their application prohibits routine use. Furthermore, the positional accuracy of some of these methods, notably those using radio signals, is relatively low (e.g. metres rather than centimetres), making them less suitable for the present application.

The aim of the present invention is to provide an improved system and method for such surveys.

When viewed from a first aspect the invention provides a system for surveying a surface to measure a physical or chemical property associated with the surface, the system comprising:

a handheld probe for measuring a physical or chemical property at a plurality of locations over a surface to be surveyed;

a video camera for capturing a sequence of frames of video data of a user holding the handheld probe while the user is using the handheld probe to survey the surface;

a depth sensing device for measuring the distance from the device to the handheld probe being used to survey the surface;

processing circuitry configured to:
identify the handheld probe from the sequence of frames of video data; and
determine the position of the handheld probe relative to the surface being surveyed by the handheld probe, using the identification of the handheld probe and the measured distance to the handheld probe; and a data recorder and/or a data transmitter for recording and/or transmitting data representative of the physical or chemical property measured by the handheld probe and data representative of the associated position of the handheld probe, when the handheld probe is determined to be less than a threshold distance from the surface being surveyed.

When viewed from a second aspect the invention provides a method of surveying a surface to measure a physical or chemical associated with the surface, the method comprising:

measuring a physical or chemical property at a plurality of locations over a surface to be surveyed using a handheld probe;

capturing a sequence of frames of video data of a user holding the handheld probe while the user is using the handheld probe to survey the surface;

measuring the distance from a depth sensing device to the handheld probe being used to survey the surface;

identifying the handheld probe from the sequence of frames of video data;

determining the position of the handheld probe relative to the surface being surveyed by the handheld probe, using the identification of the handheld probe and the measured distance to the handheld probe; and recording and/or transmitting data representative of the physical or chemical property measured by the handheld probe and data representative of the associated position of the handheld probe, when the handheld probe is determined to be less than a threshold distance from the surface being surveyed.

The present invention provides a system for and a method of surveying a surface to measure a physical or chemical property associated with (e.g. of) the surface. The system includes a handheld probe that surveys the surface and measures the physical or chemical property over the surface. The system also includes a video camera that captures video image data of a user while they are holding the handheld probe to take the measurements. The system further includes a depth sensing device that measures the distance to the handheld probe that is being used to take the measurements (and, e.g., also the user while they are holding the handheld probe and/or the surface being surveyed).

Processing circuitry of the system is used to take the video image data to identify the handheld probe being used to take the measurements. This identification of the handheld probe is then used, along with the measured distance to the handheld probe (e.g. because the depth sensor cannot identify the handheld probe per se from the data is captures), to determine the position of the handheld probe relative to the surface being surveyed by the handheld probe.

The system is arranged to record and/or transmit data representative of the physical or chemical property measured by the handheld probe and the associated position of the handheld probe (using a data recorder and/or a data transmitter), when the handheld probe is determined to be less than a threshold distance from the surface being surveyed.

Thus it will be appreciated that the system and method of the present invention allow the physical or chemical property to be coupled to the position at which this physical or chemical property was measured, using the captured measurement data of the physical or chemical property, the captured video image data and the captured distance data of the handheld probe being used to perform the survey. This allows a detailed survey to be built up of the location and measurements of the physical or chemical property, in an environment in which it may not be possible to use conventional location (e.g. GNSS) data. When the physical or chemical property comprises a contaminant, this allows the contaminant to be identified and disposed of correctly, e.g. from the contaminated environment.

The detection of many physical or chemical properties (e.g. of contaminants (e.g. using the radiation they emit)) is dependent on the distance of the probe from the source of the physical or chemical property (e.g. contaminant) being measured, such that the measurement may become unreliable (or difficult to extrapolate accurately) when the probe is too far away from the physical or chemical property being measured. Thus, the recordal and/or transmission of the data (representative of the physical or chemical property measured by the handheld probe and the associated position of the handheld probe) when the probe is close enough to the surface being surveyed (i.e. within the threshold distance), provide a quality check on the data of the measured physical or chemical property.

In addition, it will be appreciated that the invention allows hostile contaminated (e.g. enclosed) environments, previously considered too dangerous for a human surveyor to enter (e.g. for long periods), to be surveyed. This is because the system and method of the present invention help to allow the captured video data to be collected quickly without having to resort to slower manual methods. For example, in a radioactive environment, the user may be exposed to the maximum permitted personal radiation dose in a relatively short period of time, preventing a conventional manual survey to be performed. The present invention helps to reduce the radiation dose to the user by reducing the time needed to perform the survey.

However the system and method of the present invention help to allow the survey to be performed more quickly and so these more hostile environments may be accessed safely by a human surveyor. This then enables the benefits of the flexibility and dexterity of a human surveyor to be exploited, which otherwise would not be possible. Thus, while the user of the handheld probe may comprise a (e.g. autonomous) (e.g. human-shaped) robot, preferably the user is a human.

The system of the present invention may also be implemented using relatively little and inexpensive infrastructure. For example, in at least some embodiments, once the video camera and the depth sensing device have been placed in the (e.g. potentially) contaminated (e.g. enclosed) environment, the user may simply enter the (e.g. potentially) contaminated environment and perform the survey.

The handheld probe is arranged to measure a (e.g. localised) physical or chemical property (associated with a surface) at a plurality of locations over the surface to be surveyed. In a preferred embodiment the handheld probe comprises a handheld contaminant probe that is arranged to detect a concentration of a contaminant at a plurality of locations over a surface to be surveyed, e.g. in a (e.g. potentially) contaminated (e.g. enclosed) environment. Thus preferably the invention provides a system for and a method of surveying a surface (e.g. in, or having been in, a (e.g. potentially) contaminated (e.g. enclosed) environment) for the presence of a contaminant (e.g. radiation). In this embodiment the handheld contaminant probe surveys the surface and detects the concentration of the contaminant (e.g. at a plurality of locations) over the surface, and the video camera captures video image data of a user while they are holding the handheld contaminant probe to take the contaminant measurements.

Preferably the handheld (e.g. contaminant) probe is arranged to capture data representative of the measurement of the physical or chemical property (e.g. of the concentration of the contaminant) that the probe has detected, i.e. at the plurality of locations over the surface being surveyed. This captured data may then be recorded and/or transmitted by the data recorder and/or transmitter respectively, or used, e.g. by the processing circuitry, to display a representation of the measurement of the physical or chemical property (e.g. of the concentration of the contaminant) that the probe has detected, as will be described below.

The physical or chemical property may comprise any suitable and desired physical property associated with the surface, whose measurement is desired to be determined. For example, the property may comprise the thickness of a layer or layers of paint on the surface. The property may comprise presence (e.g. depth) of a reinforcing bar (re-bar) in a concrete structure.

Preferably the physical or chemical property comprises a contaminant, e.g. that is (or may be present) on the surface, and thus preferably the handheld probe comprises a handheld contaminant probe.

When the handheld probe comprises a handheld contaminant probe arranged to detect the concentration of a contaminant, the contaminant may comprise any substance whose concentration (e.g. in the enclosed environment) is desired to be determined, e.g. a hazardous chemical. The contaminant may be present on a surface to be surveyed or may be passing through a surface to be surveyed.

The handheld probe may be arranged to detect only a single type of physical or chemical property (e.g. contaminant). However in one embodiment the handheld probe is arranged to detect multiple different physical or chemical properties (e.g. contaminants). Thus the handheld probe may comprise a multi-channel probe.

In one set of embodiments the contaminant comprises radioactive material. Radioactive materials are conveniently detected by their emission of one or more of alpha particles, beta particles (electrons or positrons) and gamma radiation (photons). The alphas, betas and gammas may be present on the surface being surveyed. In addition, the radiation (e.g. gammas) may be coming through the surface (e.g. a wall) being surveyed (e.g. from a source of radioactive material behind the surface).

As will be appreciated, the method and system of the present invention are particularly suited for the detection of radioactive materials. This is because owing to the acquisition of image, distance and contamination data using the method and system of the present invention, allowing the position of the handheld probe to be determined, a survey can be performed relatively quickly, thus minimising the duration over which the handheld probe, and thus its user, are exposed to the radiation. Furthermore, as will be discussed below, instruments for the detection of radioactive materials are widely available.

The handheld (e.g. contaminant) probe could comprise any suitable handheld probe for detecting the physical or chemical property (e.g. contaminant) to be surveyed. However, as has been discussed above, the system of the present invention is particularly suitable for surveying enclosed environments which are contaminated with radioactive material(s). Therefore in one set of embodiments the handheld probe comprises a handheld radiation monitor, e.g. a Geiger counter, an alpha radiation survey meter, an ion chamber, a scintillation counter, a dose rate meter or a gamma ray spectrometer.

The type of handheld radiation monitor used could be chosen dependent upon the type of radioactive materials expected to be detected. For example, if the survey to be performed is to map the occurrence of a particular radioactive isotope which is known to decay by the emission of alpha particles, then an alpha radiation survey meter may be used. However, if the radioactive materials are not known, there may be more than one type of radioactive particles being emitted, or a general survey of the radioactivity in a (e.g. potentially) contaminated environment is desired, then a general purpose radiation monitor could be used, e.g. a combined alpha/beta radiation detector.

Typically radiation monitors detect a rate of decay of the radioactive materials, e.g. counts per second, and thus in one set of embodiments the data captured by the handheld radiation monitor comprise a rate which is representative of the concentration of the contaminant.

In one set of embodiments the handheld radiation monitor is arranged to detect the energy of the radioactive particles, e.g. preferably the handheld radiation monitor comprises a radiation spectrometer. In this set of embodiments preferably the data captured by the handheld radiation monitor comprise data representative of the energy of the radioactive particles detected by the handheld radiation monitor. This captured data may then be recorded and/or transmitted by the data recorder and/or transmitter respectively, or used, e.g. by the processing circuitry, as is appropriate.

Preferably the handheld probe is arranged to be moved between different locations (i.e. over the surface) by the user, e.g. a human, in order to perform the survey of the physical or chemical property (e.g. contaminant). Although the probe is handheld, it may form part (e.g. a component) of a larger (e.g. portable) detector that may be arranged to be pushed, dragged or wheeled (e.g. through the enclosed environment), e.g. if the detector is too large or heavy to carry, or the detector may be arranged to be carried in a carrying device, e.g. a rucksack.

The surface to be surveyed may comprise any suitable and desired surface, e.g. on or coming through which the physical or chemical property (e.g. contamination) is present. In one set of embodiments the surface comprises a surface in an enclosed environment. Preferably the surface comprises a surface of a structural component of the enclosed environment, e.g. a wall, a floor, a ceiling, a window or a door, or a surface of an object in the enclosed environment, e.g. a piece of furniture, equipment, etc.

In another set of embodiments the surface comprises the surface of a person (e.g. their clothes, (e.g. exposed) skin and/or hair) or an object in (or having (e.g. recently) been in) a (e.g. potentially) contaminated environment. The monitoring of clothing and skin surfaces (known as "frisking") of people working in (e.g. potentially) contaminated environments is performed to establish that when the workers leave a (e.g. potentially) contaminated location (e.g. in an enclosed environment), their clothes and skin are free from contamination (and if not, they can be assessed so that the contamination may be removed).

Conventionally, frisking places priority on monitoring particular areas of a worker that have the highest likelihood of contamination, e.g. hands, soles of shoes and contact points such as knees and elbows. This may then be followed by an overall scan of the worker. The process is rarely documented fully and may often not be as complete as is desired.

The task of frisking, while not necessarily needing (and often preferred not) to be performed in the enclosed environment in which the object or person was (e.g. potentially) exposed to the contaminant, presents similar challenges of dexterity and flexibility when performing a comprehensive survey as those faced in an enclosed environment. It will thus be appreciated that the system and the method of the present invention are particularly suited to this task, with the collection of the concentration and location data enabling an audit to be performed of the frisking.

The video camera is arranged to capture a sequence of frames of (e.g. visible) video image data of a user holding the handheld probe while the user is using the handheld probe to survey the surface, i.e. at the plurality of locations over the surface that the handheld probe is measuring the physical or chemical property (e.g. detecting the concentration of the contaminant). This captured sequence of frames of video data is then used (by the processing circuitry) to identify the handheld probe, in order to determine (with the distance measured to the handheld probe) the position of the handheld probe relative to the surface being surveyed by the handheld probe (e.g. by using the distance measurement at the (e.g. two-dimensional) location corresponding to the identified handheld probe). The captured sequence of frames of video data may also be recorded and/or transmitted by the data recorder and/or transmitter respectively, e.g. to keep a visual record of the survey.

The video camera could track the user by moving its field of view, e.g. by rotating about one or more axes, so to keep the user (and preferably also the handheld probe) within its field of view, e.g. by maintaining the user (or the handheld probe) at the centre of its field of view. This could be done manually, e.g. by a user operating the video camera either in situ or remotely, or it could be done automatically, e.g. using image recognition software.

However in one set of embodiments the video camera has a fixed field of view, e.g. the video camera is stationary, and is arranged to have a suitably wide angle lens in order to view the user (and, e.g., the handheld probe) across a range of positions, e.g. on the surface to be surveyed. If necessary the video camera is moved to a different position in order to survey a different part of the environment, e.g. different surfaces or portions of surfaces within the environment, or the system may comprise a plurality of video cameras each located in different parts of the environment. The sequence of frames of video image data captured at each position of the video camera may then be combined (e.g. stitched together) to generate a sequence of frames of video image data of the whole of the surface being surveyed.

Thus preferably the video camera (and preferably also the depth sensing device) remain in the same position while the surface is being surveyed by the user using the handheld probe. Preferably the video camera is located between 4 m and 5 m from the surface to be surveyed. This helps to provide a reasonably large field of view (and thus area of the surface to be surveyed) while providing sufficient detail in the captured sequence of frames of video image data to identify the handheld probe and, e.g., to perform the skeletal tracking of the user.

The video camera could comprise any suitable camera for acquiring images, e.g. with a field of view having a wide enough angle to survey the required (e.g. part of the) surface. The (e.g. enclosed) environment may already have such a video camera in situ, e.g. a closed circuit television (CCTV) camera. However, in one set of embodiments the system comprises a dedicated video camera.

Preferably the video camera and the depth sensing device are part of the same (e.g. integrated) device, e.g. preferably the system comprises an integrated device comprising the video camera and the depth sensing device. Preferably the video camera and the depth sensing device are co-located (e.g. as much as physically possible). This helps with the ease of use of the system and with the alignment of the sequence of frames of video image data and the distance measurements determined by the depth sensing device, in order to pair the identified handheld probe with the measured distance thereto.

The system also includes a depth sensing device that is used to measure the distance from the depth sensing device to the handheld probe being used to survey the (e.g. potentially contaminated) surface (and preferably also to measure the distance from the depth sensing device to the user who is using the handheld probe to survey the surface). The depth sensing device may be any suitable and desired device that is able to determine the distance to an object. In one embodiment the depth sensing device comprises a time of flight camera. Determining the time of flight (e.g. of light emitted by the camera) enables the distance to an object from the camera to be determined.

Preferably the depth sensor comprises an electromagnetic (e.g. light) source and a time of flight sensor. The electromagnetic (e.g. infrared) source may comprise a structured light projector that uses a laser to project a pattern onto the user and the surface. Distortions that are detected in the pattern are interpreted as depth changes.

Preferably the depth sensing device (e.g. the time of flight camera) is arranged to determine the respective distance to (e.g. each of the) objects in the field of view of the depth sensing device (e.g. in the image captured by the time of flight camera). Preferably the data captured by the depth sensing device comprises an array of data values (i.e. representative of the respective distance a plurality of points) over the field of view of the depth sensing device (e.g. for each frame of data captured by the depth sensing device). Thus preferably the depth sensing device (e.g. like the video camera) is arranged to capture a sequence of (e.g. arrays of) distance measurements from the depth sensing device to the handheld probe being used to perform the survey (and preferably also to the user performing the survey and the surface being surveyed).

Preferably the field of view of the depth sensing device contains (i.e. is at least as large as) the field of view of the video camera. Thus preferably the depth sensing device is arranged to determine the respective distance to each of the objects in the image captured by the video camera. Preferably the time of flight camera comprises a wide angle camera (e.g. is arranged to have a suitably wide angle lens to survey the required (e.g. part of the) surface).

The depth sensing device (e.g. time of flight camera) could track the user by moving its field of view but preferably the depth sensing device has a fixed field of view, e.g. the depth sensing device is stationary. Preferably the time of flight camera is substantially co-located with (e.g. integrated into the same device as) the video camera. This helps the captured sequence of frames of video data to be used with the distances determined by the depth sensing device by the processing circuitry to determine the (e.g. three-dimensional) position of the handheld probe (e.g. by using the distance measurement at the (e.g. two-dimensional) position determined from the frames of video data at which the handheld probe has been identified).

The data generated by the video camera and the depth sensing device (and, e.g., the handheld probe) are captured for use by the processing circuitry. Preferably one or more (e.g. all) of the handheld probe, the video camera and the depth sensing device are arranged to generate and, e.g., provide to the processing circuitry, separate respective data streams.

In one embodiment the handheld probe, the video camera and/or the depth sensing device are arranged to capture their respective data (i.e. the measurement(s) of the physical or chemical property (e.g. the concentration of the contaminant), the sequence of frames of video data and the data for determining the distance from the depth sensing device to the handheld probe respectively) continuously while the survey is being performed (i.e. while the user is using the handheld probe to measure the physical or chemical property (e.g. to detect the concentration of the contaminant)).

Thus preferably the method is performed repeatedly to capture the necessary plurality of pieces of data in order to determine a plurality of positions of the handheld probe relative to the surface being surveyed by the handheld probe, e.g. for the whole of the survey being performed, and the data recorder and/or the data transmitter are arranged to record and/or transmit data representative of the physical or chemical property (e.g. of the concentration of the contaminant) measured by the handheld probe and data representative of the associated position of the handheld probe, for each of the plurality of locations over the surface being surveyed at which the handheld probe is determined to be less than a threshold distance from the surface being surveyed.

The respective data captured when the handheld probe is determined to be less than the threshold distance from the surface being surveyed may then be the (e.g. only) data processed, recorded and/or transmitted (as appropriate), e.g. with any other data being discarded. Alternatively, as discussed below, all of the data captured may be processed, recorded and/or transmitted, with the data for which the handheld probe is determined to be less than the threshold distance from the surface being surveyed being identified (e.g. flagged or tagged) as having been captured when the handheld probe was determined to be less than the threshold distance from the surface being surveyed, e.g. the data is identified (e.g. in the recorded and/or transmitted data) as those for which the physical or chemical property measurements (e.g. the detected contaminant concentrations) are valid.

The data recorder, the data transmitter and/or the processing circuitry (as is applicable) may obtain or access the data detected and, e.g., captured by the handheld probe the video camera and/or the depth sensing device in any suitable and desired way. The handheld probe (or, e.g., the detector of which it forms a part), the video camera and/or the depth sensing device may comprise a memory (e.g. a hard disk drive or solid state memory) for storing their respective captured data (e.g. locally and, e.g., temporarily) before it is used by the processing circuitry and/or the data recorder and/or the data transmitter (as appropriate).

The handheld probe (or, e.g., the detector of which it forms a part), the video camera and/or the depth sensing device may comprise a connection (e.g. a wired or wireless (e.g. Bluetooth) connection) to one or more of the data recorder, the data transmitter and/or the processing circuitry. This enables the data representative of the physical or chemical property measured (e.g. the concentration of the contaminant detected) by the handheld probe to be stored locally and/or transmitted to another part of the system (e.g. the data recorder, the data transmitter and/or the processing circuitry) as and when desired.

The data captured by the video camera and the depth sensing device are preferably associated with data representative of the time at which the respective data is captured. Preferably the video camera and the depth sensing device are synchronised with each other, e.g. the video camera and the depth sensing device may comprise a common clock. This (e.g. (common) synchronised) time stamp on the data captured by the video camera and the depth sensing device conveniently allows the captured data to be matched together, e.g. by the processing circuitry.

Preferably the data captured by the handheld probe is also associated with data representative of the time at which the respective data is captured. The handheld probe may be synchronised with the video camera and the depth sensing device. This helps to allow the captured data (representative of the physical or chemical property) to be matched to the other captured data, e.g. by the processing circuitry.

The respective time data may be provided by the handheld probe, the video camera and/or the depth sensing device (e.g. as the data is captured). Thus preferably the handheld probe, the video camera and/or the depth sensing device are arranged to record data representative of the time at which their respective data are acquired, e.g. one or more of the handheld probe, the video camera and the depth sensing device comprises a clock arranged to generate a time stamp. The video camera and the depth sensing device may comprise synchronised clocks or a common clock.

Alternatively the respective time data could be provided by the processing circuitry (e.g. when the data is received for processing), or by the data recorder and/or transmitter (e.g. as the captured (or, e.g., processed) data is output, e.g. for further processing). Thus the captured data could comprise the time data, or the time data could be generated (and then recorded and/or transmitted) separately. In this latter case, preferably the data transmitter and/or the data recorder comprises a clock arranged to generate a time stamp associated with the data that is transmitted and/or recorded.

The handheld probe may be identified from the sequence of frames of video data in any suitable and desired way (such that the position of the handheld probe may then be determined). The handheld probe may be identified using image recognition (e.g. by looking for the colour and/or shape of the handheld probe per se). In one embodiment the handheld probe comprises a particular marking (e.g. a predefined shape and/or colour) that may be used (e.g. identified by the processing circuitry) to determine the position of the handheld probe using the frames of video data. This recognisable mark may help the handheld probe to be identified easily using the sequence of frames of video image data.

Preferably the particular marking on the handheld probe comprises a colour (e.g. a coloured marker) that is contrasting to the colour of the handheld probe. In one embodiment the particular marking comprises a prominent red marker on a yellow probe. In one embodiment the particular marking comprises an illuminated marker, e.g. a light (e.g. visible or infrared) or a beacon.

In a preferred embodiment the step of identifying the handheld probe comprises identifying the user from the sequence of frames of video data (and then identifying (e.g. locating) the handheld probe using the identification of the user). For example, as will be discussed further below, if the user can be identified (and, e.g. the different parts of their body), this can be used to help locate the handheld probe in the video image data.

The user may be identified from the sequence of frames of video image data in any suitable and desired way. In a preferred embodiment the step of identifying the handheld probe comprises performing skeletal tracking of the user using the sequence of frames of video image data. In these embodiments preferably the handheld probe is identified using the skeletal tracking. Preferably the skeletal tracking of the user uses the distance data to the user. Preferably the depth sensor is arranged to measure the distance from the device to the user while the user is using the handheld probe to survey the surface, e.g. to be used to perform the skeletal tracking.

The skeletal tracking may be performed in any suitable and desired way, e.g. using Microsoft Kinect® software. Preferably the skeletal tracking is arranged to determine the (e.g. three-dimensional) position of the user's limbs, torso and head. Preferably the skeletal tracking is arranged to determine the (e.g. three-dimensional) position of the main joints of the user's limbs, torso and head (e.g. one or more of the hips, neck, knees, elbows, ankles, wrists).

The processing circuitry then preferably uses the output from the skeletal tracking to determine the (e.g. three-dimensional) position of the handheld probe relative to the surface being surveyed. The (e.g. three-dimensional) position of the handheld probe may be determined in any suitable and desired way.

The handheld probe may be identified by determining the position of a particular part of the user's body (e.g. their hand). Thus the position of the handheld probe may be assigned the position of this particular part of the user's body (e.g. if the user is instructed to hold the handheld probe in a particular hand).

However, the handheld probe may not necessarily be assigned to a particular part of the user's body. Thus, in a preferred embodiment, the method comprises (and the processing circuitry is configured to) determining the position of the handheld probe visually using the sequence of frames of video data (e.g. together with the skeletal tracking of the user).

Preferably the position of the handheld probe is determined (by the processing circuitry) by determining the position of a particular (e.g. central) part of the user's body (e.g. their neck, head or torso), (e.g. using the skeletal tracking), and then looking (e.g. analysing the sequence of frames of video data) in the vicinity (e.g. within a particular distance, e.g. 1.5 m) of the determined particular part of the user's body for the handheld probe.

Preferably the processing circuitry, when the sequence of video frames are used to determine the position of the handheld probe, is configured to look (e.g. by analysing the sequence of frames of video data) in one frame of the sequence of frames of video data for the handheld probe in the vicinity (e.g. within a particular distance, e.g. 0.5 m) of the location of the handheld probe in a previous frame of the sequence of frames of video data (e.g. the immediately previous frame in the sequence). This is a convenient way of locating the position of the handheld probe in a subsequent frame owing to the user generally only moving the handheld probe a short distance between each adjacent frame in the sequence of frames.

When the handheld probe is not identified within a particular distance of the location of the handheld probe in a previous frame of the sequence of frames of video data, preferably the processing circuitry is configured to look within a greater distance than the particular initial distance, e.g. until the handheld probe is identified or, e.g., the whole of the frame of video data has been analysed.

The position of the handheld probe relative to the surface is determined, so that it can be determined when the handheld probe is within a threshold distance from the surface being surveyed. The relative position of the handheld probe to the surface being surveyed may be determined in any suitable and desired way. Preferably the relative position is determined by determining the shortest distance between the handheld probe and the surface being surveyed by the handheld probe.

Preferably the relative position is determined by determining the position(s) of the surface being surveyed by the handheld probe. The position(s) of the surface may be determined in any suitable and desired way. For example, the position(s) of the surface may be determined (e.g. while the surface is being surveyed, at the same time as the position of the handheld probe is being determined) using the sequence of frames of video data and/or the distance(s) from the depth sensing device to the surface as determined by the depth sensing device (which, as outlined above, preferably determines the distance to all of the objects within its field of view).

However, it will be appreciated that the survey of the surface will often be performed in a manner such that the handheld probe is (e.g. directly) in front of (and thus covering) the (e.g. part of the) surface relative to which the position of the handheld probe is being determined relative to (e.g. to which it is closest). Thus preferably the method comprises (and the depth sensing device and/or the video camera are arranged to) determining the distance from the depth sensing device to the surface (to be or being surveyed). This helps the system to determine the position(s) of the surface to be (or being) surveyed, such that the position of the handheld probe relative to the surface may be determined.

This step is preferably performed as a "calibration" step, e.g. prior to the survey being performed. Preferably the step of determining the distance from the depth sensing device to the surface is performed with the user and the handheld probe absent from the field of view of the depth sensing device and/or the video camera (as appropriate). Preferably the depth sensing device and/or the video camera are used (e.g. remain) in the same position for both the "calibration" step and when the handheld probe is being used to perform the survey. This helps to simplify the process of determining the relative position of the handheld probe to the surface.

Preferably the (e.g. three-dimensional) position of the handheld probe relative to the device is determined (and then preferably transmitted and/or recorded), e.g. as well as the relative position of the handheld probe to the surface being surveyed. Thus preferably the method comprises (and the processing circuitry is configured to) determining the (e.g. three-dimensional) position of the handheld probe from the device, e.g. using the frames of video image data and the determined distance data.

Determining the (e.g. three-dimensional) position of the handheld probe helps to allow the (e.g. three-dimensional) position of the physical or chemical property (e.g. contaminant) detected by the handheld probe to be determined. Thus preferably the method comprises determining the positions of the plurality of locations over the surface at which a physical or chemical property was measured (e.g. a concentration of a contaminant was detected) using the determined positions of the handheld probe.

The (e.g. three-dimensional) position(s) (relative to the device) of the handheld probe (and thus of the physical or chemical property (e.g. contaminant) being measured) may be determined in any suitable and desired way, e.g. in a similar manner as outlined above for the position(s) relative to the surface. For example, the position relative to the device may be determined as part of the process of determining the position relative to the surface, e.g. the position relative to the device may be determined in order to determine the position relative to the surface or using the position relative to the surface. The position(s) relative to the device may be determined separately from the position(s) relative to the surface.

In one embodiment the position(s) of the handheld probe relative to the device is determined in two dimensions, e.g. over the surface being surveyed, e.g. using the frames of video image data. In another embodiment the position(s) of the handheld probe relative to the device is determined in three dimensions, e.g. using the distances to the user determined by the depth sensing device, the frames of video image data and/or the skeletal tracking of the user.

The determined position(s) of the handheld probe relative to the device are preferably recorded and/or transmitted with the other recorded and/or transmitted data, i.e. when the handheld probe is determined to be less than a threshold distance from the surface being surveyed. Preferably the determined position(s) of the handheld probe relative to the device are associated with the data representative of the physical or chemical property measured (e.g. the concentration of the contaminant detected) by the handheld probe, e.g. using time stamp data, such that the positions of the plurality of locations over the surface at which a physical or chemical property was measured (e.g. at which a concentration of a contaminant was detected) may be (and preferably is) determined.

Preferably the skeletal tracking (and, e.g., the determining of the position(s) of the handheld probe (relative to the device and/or the surface)) is performed in real time, i.e. while the user is performing the survey using the handheld probe. This allows feedback (e.g. of where the handheld probe has been moved and/or whether it was close enough to the surface to make a valid measurement of the physical or chemical property (e.g. of the potential contaminant)) to be provided to the user as they are performing the survey, as will be discussed in more detail below.

The determination of the relative position of the handheld probe to the surface being surveyed, by the processing circuitry, using the skeletal tracking of the user, enables, e.g. the processing circuitry, to determine when the handheld probe is less than a threshold distance from the surface being surveyed. The data recorder and/or transmitter then records and/or transmits (as appropriate) data representative of the physical or chemical property measured (e.g. the concentration of the contaminant detected) by the handheld probe and data representative of the associated position of the handheld probe. This allows a quality check on the survey to be performed, e.g. because when the handheld probe is greater than the threshold distance from the surface being surveyed the physical or chemical property (e.g. the concentration of the contaminant) may not be able to be measured sufficiently accurately.

Thus, preferably the method comprises (and the processing circuitry is configured to) determining when the handheld probe is less than a threshold distance from the surface being surveyed (and then the data recorder and/or the data transmitter recording and/or transmitting the data representative of the physical or chemical property measured (e.g. of the concentration of the contaminant detected) by the handheld probe and the data representative of the associated position of the handheld probe, when the handheld probe is determined to be less than the threshold distance from the surface being surveyed). Preferably the threshold distance is assessed against the shortest distance between the handheld probe and the surface being surveyed by the handheld probe.

The threshold distance may be any suitable and desired distance. Preferably the threshold distance is less than 20 cm, e.g. less than 10 cm, e.g. approximately 5 cm. However, it will be appreciated that the threshold distance may depend on a number of factors, including the type of handheld probe, the nature of the survey, the time take to perform the survey, the resolution of the physical or chemical property (e.g. contaminant concentration) data, etc. The threshold distance may therefore differ for different such factors.

The data representative of the physical or chemical property measured (e.g. the concentration of the contaminant detected) by the handheld probe and the data representative of the associated position of the handheld probe may be indicated to be (e.g. "valid") data that has been collected when the handheld probe is determined to be less than a threshold distance from the surface being surveyed, in any suitable and desired way.

In one embodiment, the data representative of the physical or chemical property measured (e.g. the concentration of the contaminant detected) by the handheld probe and the data representative of the associated position of the handheld probe are only transmitted when the handheld probe is determined to be less than a threshold distance from the surface being surveyed. Thus, in this embodiment any data representative of the physical or chemical property measured (e.g. the concentration of the contaminant detected) by the handheld probe and the data representative of the associated position of the handheld probe that are captured when the handheld probe is determined to not be less than a threshold distance from the surface being surveyed is not recorded and is not transmitted. This means that any data that is recorded and/or transmitted may be assumed to have been captured when the handheld probe was determined to be less than a threshold distance from the surface being surveyed.

However, it will be appreciated that this method of selecting the data to be recorded and/or transmitted does not allow an audit of the data to be performed, e.g. in the event of a system error. Therefore, in another embodiment, all of the data representative of the physical or chemical property measured (e.g. the concentration of the contaminant detected) by the handheld probe and the data representative of the associated position of the handheld probe that is captured are recorded and/or transmitted. Preferably the method comprises (and the data transmitter and/or data recorder is arranged to) recording and/or transmitting an indication of when the handheld probe was determined to be less than a threshold distance from the surface being surveyed, e.g. associated with the data representative of the physical or chemical property measured (e.g. the concentration of the contaminant detected) by the handheld probe and the data representative of the associated position of the handheld probe.

The indication (e.g. generated by the processing circuitry) may simply comprise the position of the handheld probe (e.g. relative to the device and/or the surface), e.g. such that a different threshold distance may be applied to the data subsequently, or such that the captured data may be extrapolated to areas of the surface that were missed by the survey or for which the handheld probe was not quite close enough to the surface for it to be a valid measurement.

Preferably the indication comprises a flag associated with the data representative of the physical or chemical property measured (e.g. the concentration of the contaminant detected) by the handheld probe and the data representative of the associated position of the handheld probe, e.g. with the flag being recorded and/or transmitted when the handheld probe was determined to be less than (or, alternatively, greater than) a threshold distance from the surface being surveyed. The flag enables the "valid" data to be identified easily.

The data representative of the position of the handheld probe, associated with the data representative of the physical or chemical property measured (e.g. the concentration of the contaminant detected) by the handheld probe, that is transmitted and/or recorded may be the position of the handheld probe relative to the device and/or the surface being surveyed.

The data transmitter and the data recorder may be any suitable data transmitter and data recorder. For example, the data recorder preferably comprises a memory for storing the captured data (e.g. locally and, e.g., temporarily) for subsequent downloading or transmission. The memory may comprise a hard disk drive or solid state memory such as a random access memory (RAM). The memory may be permanent or removable. The data recorded on the data recorder may then be transferred manually from the portable device, for example by removing the memory, e.g. a memory card, or connecting a detachable cable such as a USB cable. Alternatively the data recorded may be transmitted by the data transmitter.

The data transmitter preferably comprises a connection (e.g. a wired or wireless (e.g. WiFi, Bluetooth, RF, infra-red, etc.) connection) to a (e.g. remote) computer for transmitting the data. Preferably the computer is arranged to record and/or further analyse the transmitted data.

The system preferably comprises a feedback device arranged to provide feedback information to the user, e.g. regarding the survey being performed. Preferably the feedback information is provided in real time, i.e. while the survey is being performed. Preferably the feedback information is provided when a particular criterion or criteria (e.g. based on the way the user is performing the survey) are satisfied.

In one embodiment feedback information is provided when the handheld probe is determined to be more than a threshold distance from the surface being surveyed. This helps to alert the user to retain the handheld probe within the threshold distance from the surface.

In one embodiment feedback information is provided when the handheld probe cannot be identified, e.g. by the processing circuitry, e.g. using the frames of video image data. This may be when the handheld probe has been moved out of the field of view of the video camera and/or the depth sensing device, and/or when the handheld probe (or a marking thereon) has been obscured, e.g. by the user or the handheld probe being rotated such that the marking is out of view.

In one embodiment feedback information is provided when the handheld probe is being moved too quickly over the surface being surveyed. In one embodiment feedback information is provided when the user has failed to survey an area of the surface being surveyed (e.g. when the user has surveyed adjacent or surrounding areas of the surface). Thus the feedback information may comprise a warning (e.g. dependent on the feedback device) to alert the user to the particular criterion or criteria that has been satisfied, e.g. owing to the way in which they are performing the survey. The feedback information may also be provided when the user has completed the survey of the surface, e.g. when the user has moved the handheld probe across the whole area of the surface, e.g. within the threshold distance.

The feedback information may comprise any suitable and desired information, e.g. audio, visual or haptic information. In one embodiment the handheld probe comprises the feedback device, e.g. the handheld probe may be arranged to provide an audio, visual or haptic signal, e.g. when a particular criterion or criteria are satisfied. In one embodiment the system comprises a separate feedback device (e.g. in a component comprising the processing circuitry) arranged to provide the feedback information.

In one embodiment the feedback device comprises a light or display screen (or a projector) arranged to provide a visual signal, when a particular criterion or criteria are satisfied. The display screen may, for example, be provided on the handheld probe, on a head-up display that the system may comprise for the user to wear or on a separate computer that the system may comprise, e.g. which comprises the processing circuitry. The display may be projected onto a surface, e.g. the surface being surveyed. This may be helpful in identifying to the user of the handheld probe the areas of the surface that they have surveyed (e.g. validly).

When the feedback device comprises a display screen or projector, preferably the display screen (or projector) is arranged to display (and thus preferably the feedback information comprises) a representation of the surface being surveyed (e.g. with the same field of view as the video camera and/or the depth sensing device). Preferably the display screen (or projector) is arranged to display (e.g. as a particular colour or luminous intensity) the point(s) on the surface that have been surveyed by the handheld probe.

Preferably the display screen (or projector) is arranged to display the user performing the survey. For example, the display screen (or projector) may show the frames of video image data, overlaid with representation(s) of additional data, as is suitable and desired.

Preferably the display screen (or projector) is arranged to display (e.g. as a particular colour or luminous intensity) the physical or chemical property (e.g. the concentration of the contaminant) measured by the handheld probe at each of the points on the surface that have been surveyed. This representation of the physical or chemical property (e.g. the concentration of the contaminant) (e.g. the colouring) may be chosen (or may be varied) depending on the range and/or the standard deviation of the (e.g. concentration) measurements acquired by the handheld probe.

Preferably the display screen (or projector) is arranged to display (e.g. as a particular colour or luminous intensity) the point(s) on the surface that have been surveyed by the handheld probe when the handheld probe was within the threshold distance from the point(s) on the surface being surveyed. Thus the display may reflect the data that is recorded and/or transmitted when the handheld probe is determined to be less than a threshold distance from the surface being surveyed.

The display screen (or projector) may only show the point(s) (and, e.g., the physical or chemical property (e.g. concentration of the contaminant) at these points) that have been surveyed validly or the display screen (or projector) may show these point(s) in a different colour to the point(s) that have been surveyed when the handheld probe was not within the threshold distance from the point(s) on the surface being surveyed. This helps the user to see where they have surveyed the surface correctly and where they still need to survey (and/or need to repeat to survey the surface validly).

The display that is displayed on the display screen (or by the projector) may be recorded. Additionally or alternatively the display may be recreated (or prepared in an alternative format) from the data acquired that is transmitted and/or recorded. This enables a visual audit report of the survey to be produced, e.g. (2D or 3D) representation (e.g. map) of the determined position(s) (and, e.g., concentration(s)) of the physical or chemical property measured (e.g. the contaminant) on the surface that was surveyed. This may help with the removal and disposal of any contaminant that has been detected by the survey.

Thus preferably the processing circuitry is arranged (and the method comprises) to compose (and output for display) a diagrammatic representation of the surface being surveyed. The diagrammatic representation preferably includes the data displayed as described above, e.g. for each of the plurality of locations of the surface surveyed. Thus preferably the processing circuitry is arranged (and the method comprises) to combine the physical or chemical property (e.g. the contaminant concentration) measurements and the associated determined positions of the handheld probe (e.g. using the time stamp data), for the purposes of display, e.g. for each of the plurality of locations over the surveyed surface.

Preferably the data is displayed at a resolution corresponding to a position accuracy of approximately 5 cm. This resolution may depend on one or more of the resolution at which the frames of video image data were captured by the video camera, the resolution at which the distance data were captured by the depth sensing device and/or the position resolution of the handheld probe.

In one embodiment the feedback device comprises a speaker arranged to provide an audio signal, when a particular criterion or criteria are satisfied, e.g. when the handheld probe is moved further away from the surface being surveyed than the threshold distance.

In one embodiment the feedback device comprises a vibrator (e.g. in the handheld probe) arranged to provide a haptic signal (e.g. a vibration), when a particular criterion or criteria are satisfied, e.g. when the handheld probe is moved further away from the surface being surveyed than the threshold distance.

As mentioned above, the system of the present invention may be used to perform a "frisking" survey of an individual who or object that has been in an environment that may contain a contaminant. In this embodiment the surface to be surveyed comprises the surface of the person (e.g. their clothes, (e.g. exposed) skin and/or hair) or the surface of the object in (or that has (e.g. recently) been in) the potentially contaminated environment.

When a "frisking" survey is performed, the "calibration" step of determining the positions of the surface to be surveyed may not need to be performed. In a preferred embodiment, when a person is being "frisked", the position(s) of the surface to be (or being) surveyed are determined by performing skeletal tracking of the person being surveyed. Thus preferably the depth sensing device is arranged to determine the distance from the device both to the user performing the survey and the person being surveyed (and the handheld probe), and the processing circuitry is configured to perform skeletal tracking of the user performing the survey and the person being surveyed using the sequence of frames of video data (of the user using the handheld probe to survey the surface of the person) and, e.g., the determined distances to the user and to the person being surveyed.

Preferably the video camera and the depth sensing device are arranged (e.g. positioned) such that both the user performing the survey and the person or object being surveyed ("frisked") are in the field of view of both the video camera and the depth sensing device. Thus the person or object being scanned may be turned around (e.g. to face away from the video camera and the depth sensing device) in order to scan their back (or vice versa for their front).

The positions that are determined for the locations of the surface of the person being surveyed may be determined from the distance measurements that are acquired by the depth sensing device or may be determined from the skeletal tracking of the person being surveyed. For the latter, once the skeletal tracking has been performed, the processing circuitry may form a wrapper around the person, to estimate the location of their surface (i.e. of their skin, hair and clothing as appropriate).

Thus, for this "frisking" embodiment, preferably the data recorded and/or transmitted comprises data representative of the physical or chemical property measured (e.g. the concentration of the contaminant detected) by the handheld probe, data representative of the associated position of the handheld probe and data representative of the associated (e.g. skeletal) position of the person being survey, when the handheld probe is determined to be less than the threshold distance from the surface of the person being surveyed.

Where applicable, all of the preferred and/or optional features outlined above for other embodiments apply equally to this "frisking" embodiment. For example, a visual representation of the survey may be displayed on a display screen. This may show the body of the person being scanned and an indication of the physical or chemical property (e.g. the concentration of the contaminant) at the locations that have been surveyed, e.g. along with an indication of when the handheld probe was determined to be less than the threshold distance from the surface of the person being surveyed.

It will also be appreciated that the system and method of the present invention may be adapted to be used as a training tool, e.g. to train users how to perform a survey of a (e.g. potentially hazardous) physical or chemical property (e.g. contaminant)). This may help them to learn how to perform such surveys in a safe environment. With such training, a handheld probe is still used to measure a physical or chemical property over a surface to be surveyed, however the physical or chemical property may comprise a substance or material that has been (e.g. strategically) positioned (e.g. solely) for the purposes of training.

Using the system and method of the present invention in this way may then be used to identify, for example, whether or not a user is holding the probe close enough to the surface being surveyed (i.e. within the threshold distance) and/or whether the user is covering the whole area of the surface to be surveyed. This may thus train a user in how to perform a survey efficiently.

Certain embodiments of the invention will now be described, by way of example only, with reference to the accompanying drawings, in which.

The monitoring of surfaces for contamination in enclosed environments such as buildings is a frequent task in health physics and remediation scenarios, notably nuclear facilities. In particular, the presence of small, contaminating materials, e.g. radioactive materials, can result in complications with the demolition of a building and the disposal of the resulting waste. Mapping contamination on such surfaces therefore allows areas of contamination to be identified to allow the contaminating materials to be disposed of correctly.

Figure 1:
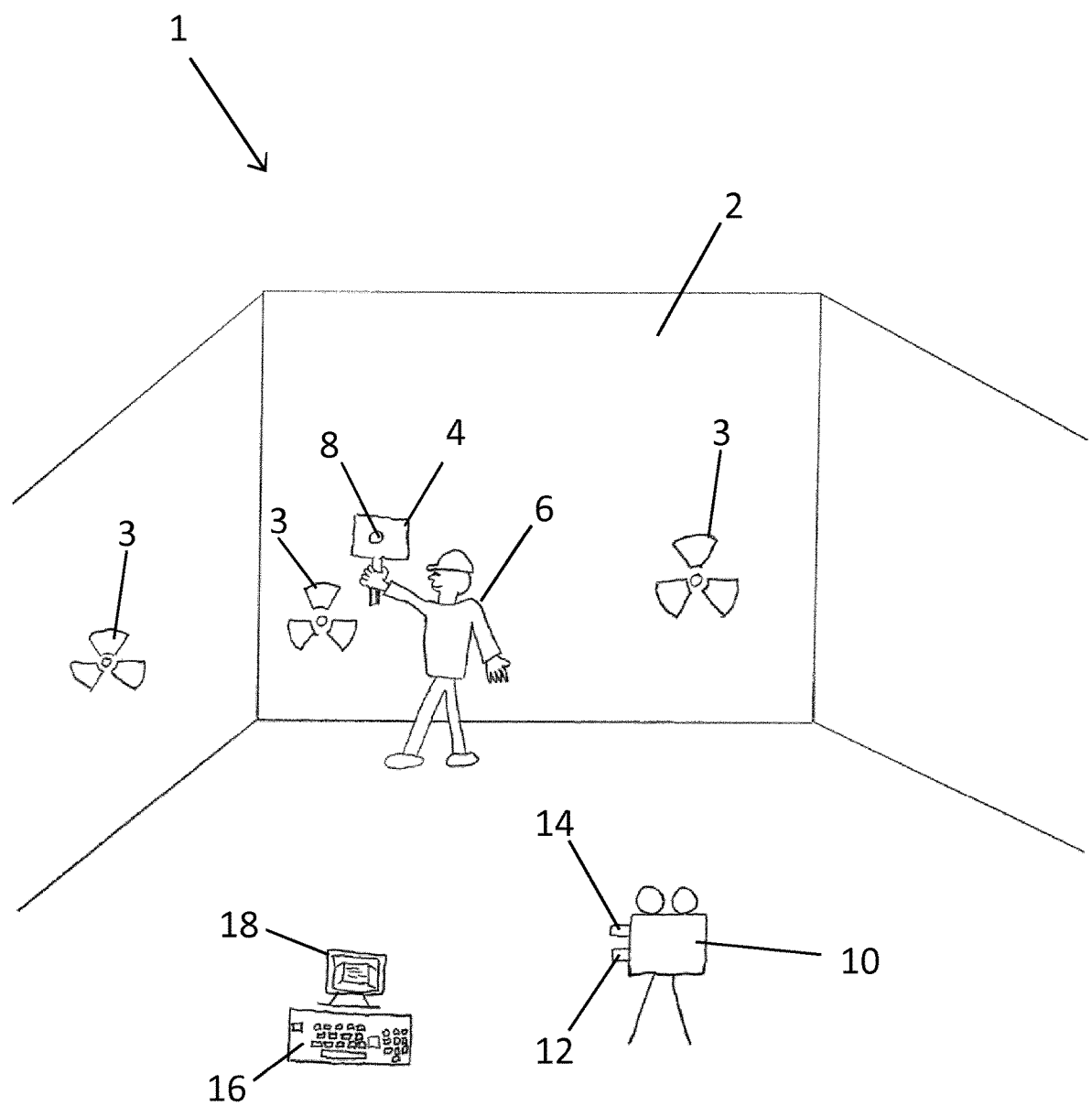
FIG. 1 shows an overview of a system in use in an enclosed environment according to an embodiment of the present invention.

FIG. 1 shows an overview of a system according to an embodiment of the present invention, in an enclosed environment 1 to be surveyed. In this embodiment, the enclosed environment 1 is inside a building in a nuclear facility, in which positioning technology such as GNSS cannot be used. Surfaces 2 in the enclosed environment 1 may contaminated with radioactive material 3, the position and concentration of which needs to be determined.

The system includes a handheld radiation probe 4 arranged to measure the concentration of radiation in the vicinity of the handheld radiation probe 4. The handheld radiation probe 4 is controlled by a user 6 and has on its housing a coloured patch or illuminated target 8 to visually identify the handheld radiation probe 4. The system also includes a skeletal tracking device 10 that includes an integrated video camera 12 and depth sensing device 14.

The skeletal tracking device 10 is positioned in the enclosed environment 1 such that the video camera 12 can acquire frames of video image data, and the depth sensing device 14 can acquire distance data, of the surface 2, the user 6 and the handheld radiation probe 4. The system also includes a computer 16 that has a display screen 18. The display screen 18 may be a conventional computer screen that is (e.g. physically) connected to the other components of the computer 16 or may be a head-up display for the user 6 to wear, for example. If the display screen 18 is provided as a head-up display, this may be connected wirelessly to the other components of the computer 16.

Figure 2:
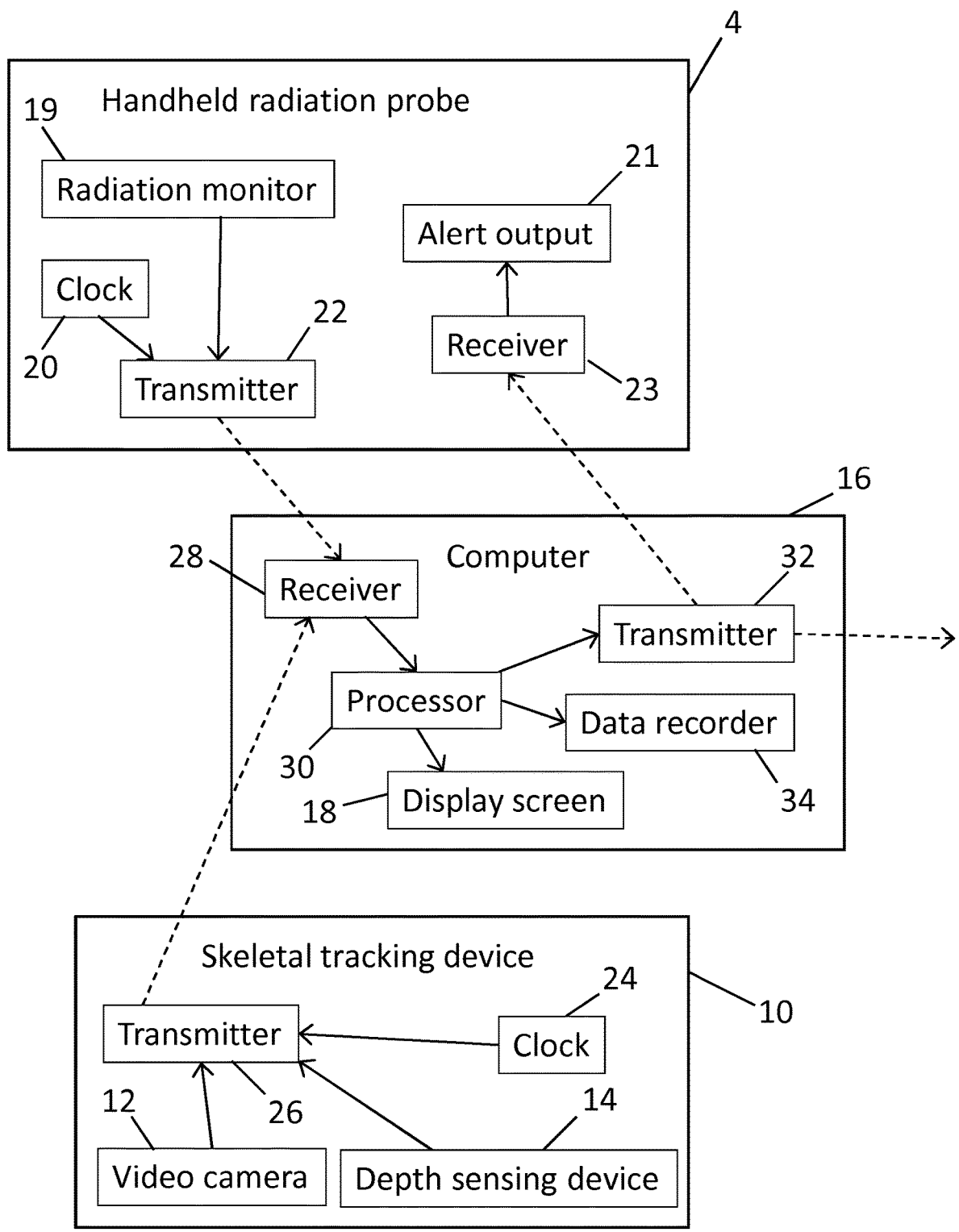
FIG. 2 shows schematically the components of the system shown in FIG. 1 according to an embodiment of the present invention.

FIG. 2 shows schematically the components of the system shown in FIG. 1.

The handheld radiation probe 4 includes a radiation monitor 19 arranged to detect the radiation concentration measurements (e.g. the count-rates) of the radioactive material (e.g. alphas, betas, gammas) present (i.e. on or coming through the surface 2 to be surveyed). The handheld radiation probe 4 also includes a clock 20 arranged to generate a time stamp to be associated with each radiation concentration measurement captured by the radiation monitor 19.

The handheld radiation probe 4 also includes a radio (e.g. Bluetooth®) transmitter 22 that enables wireless communication with the computer 16 to allow data acquired by the handheld radiation probe 4 to be transmitted wirelessly to the computer 16. The radiation monitor 19 and the clock 20 are connected to the transmitter 22 so that they can transfer their data to the transmitter 22.

The handheld radiation probe 4 further includes an output 21 to generate an alert (e.g. a visual, audio or haptic signal) for the user 6 and a Bluetooth receiver 23 arranged to receive signals wirelessly from the computer. The alert output 21 and the receiver 23 are connected to each other so that the receiver 23 can control the alert output 21.

The skeletal tracking device 10 includes a clock 24 arranged to generate a time stamp to be associated with each of the frames of video image captured by the video camera 12 and with each of the distance measurements captured by the depth sensing device 14. The skeletal tracking device 10 also includes a Bluetooth transmitter 26 that enables wireless communication with the computer 16 to allow data acquired by the video camera 12 and the depth sensing device 14 to be transmitted wirelessly to the computer 16.

The computer 16 includes the display screen 18 (which, as outlined above, may be connected physically or wirelessly to, and in the vicinity of or remote from, the other components of the computer 16). The computer 16 also includes a receiver 28 arranged to receive wirelessly the data acquired and transmitted by the handheld radiation probe 4 and the skeletal tracking device 10, and a processor 30 arranged to process these data which is connected to the receiver 28, i.e. using skeletal tracking software that is executed by the processor 30. The computer 16 further includes a data transmitter 32 arranged to transmit the processed data (and other signals) from the computer 16, and a recorder 34 (e.g. memory) arranged to store the processed data, as will be described.

Operation of the system will now be described with reference to FIGS. 1 and 2, as well as the flow chart of FIG. 3 which details the main steps of a method in accordance with an embodiment of the invention.

Figure 3:
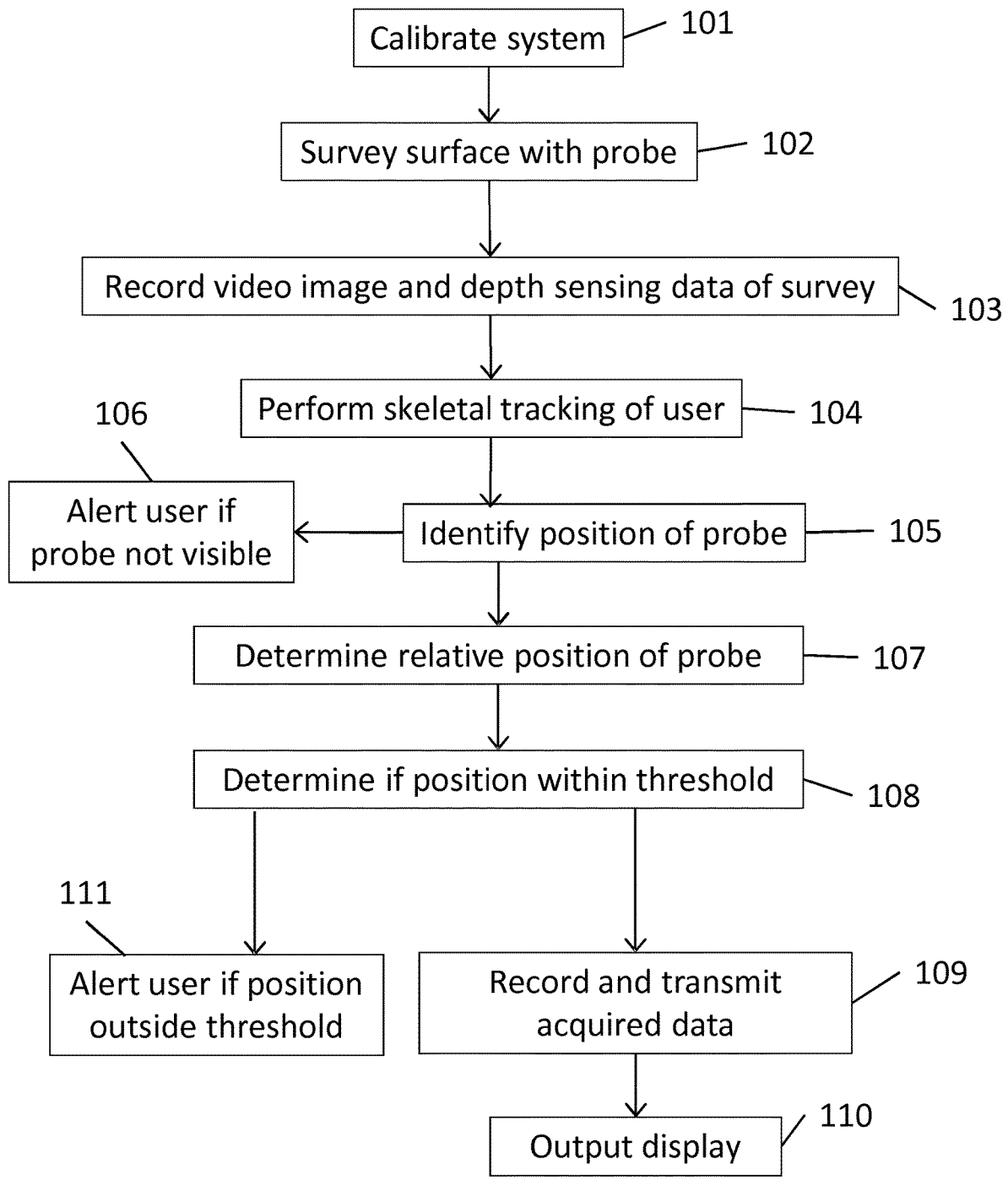
FIG. 3 shows a flow chart of the user of the system shown in FIGS. 1 and 2 according to an embodiment of the present invention.

The first task, before any determination of the location and concentration of the radioactive material 3 in the enclosed environment 1 can be taken, is to calibrate the video camera 12 and depth sensing device 14 (step 101, FIG. 3). This enables the position of the surface 2 to be surveyed in the enclosed environment 1, relative to the skeletal tracking device 10, to be determined.

The calibration is performed by acquiring frames of video image data of and distance data to the surface using the video camera 12 and the depth sensing device 14 respectively. These data are acquired when the user 6 and the handheld radiation probe 4 are not present within the field of view of either the video camera 12 or the depth sensing device 14. The acquired frames of video data and the distance data are transferred to computer 16 via the transmitter 26 of the skeletal tracking device 10 and the wireless receiver 28 of the computer 16. This enables the positions of the whole of the surface 2 to be surveyed to be determined by the processor 30 executing the skeletal tracking software.

Also performed during calibration is the step of synchronising the clock 20 of the handheld radiation probe 4 and the clock 24 of the skeletal tracking device 10. This enables the data captured by these components to be matched together, so that the radiation concentration measurements captured by the handheld radiation probe 4 can be associated with respective positions determined from the data captured by the skeletal tracking device 10.

Once the calibration has been performed, the system can be used to collect data on the location and concentration of the radioactive material 3 in the enclosed environment 1 (i.e. on or coming through the surfaces 2 in the enclosed environment 1). The skeletal tracking device 10 is retained in the same position as it was for the calibration (so that no further calibration or transformation of the position data needs to be performed), with the surface 2 in the enclosed environment 1 to be surveyed within its field of view.

As shown in FIG. 1, a user 6 uses the handheld radiation probe 4 to survey the surface 2 in the enclosed environment 1 (step 102, FIG. 3) and the radiation monitor 19 of the handheld radiation probe 4 detects the concentration (e.g. count-rates) of any radioactive material 3 (e.g. alphas, betas, gammas) present (i.e. on or coming through the surface 2) at the various locations surveyed on the surface 2. Each piece of concentration data captured by the radiation monitor 19 is associated with a respective time stamp generated by the clock 20 of the handheld radiation probe 4. The concentration data along with the associated time stamps are transmitted by the transmitter 22 of the handheld radiation probe 4 to the computer 16, where the data are received by the receiver 28 of the computer 16.

At the same time as the radiation concentration data is being captured by the handheld radiation probe 4, the skeletal tracking device 10 is used to acquire frames of video image data of and distance data to the user 6 of the handheld radiation probe 4 as it is being used to survey the surface 2, using the video camera 12 and depth sensing device 14 respectively of the skeletal tracking device 10 (step 103, FIG. 3). The user 6 is instructed to hold the handheld radiation probe 4 such that the coloured patch 8 on the housing of the handheld radiation probe 4 is visible to the video camera 12, and such that the handheld radiation probe 4 is moved within a maximum ("threshold") distance of 5 cm from the surface 2 being surveyed. This helps to maintain a uniform quality of data capture.

Each frame of video image data captured by the video camera 12 and each piece of distance data captured by the depth sensing device 14 is associated with a respective time stamp generated by the clock 24 of the skeletal tracking device 10. The frames of video image data and the distance data, along with the associated time stamps, are transmitted by the transmitter 26 of the skeletal tracking device 10 to the computer 16, where the data are received by the receiver 28 of the computer 16.

In real time, while the survey is being performed, the processor 30 of the computer 16 processes the video image data and the distance data it has received from the receiver 28 of the computer 16, to perform skeletal tracking of the user 6 performing the survey (step 104, FIG. 3). The process will be described in further detail with reference to FIG. 4.

Figure 4:
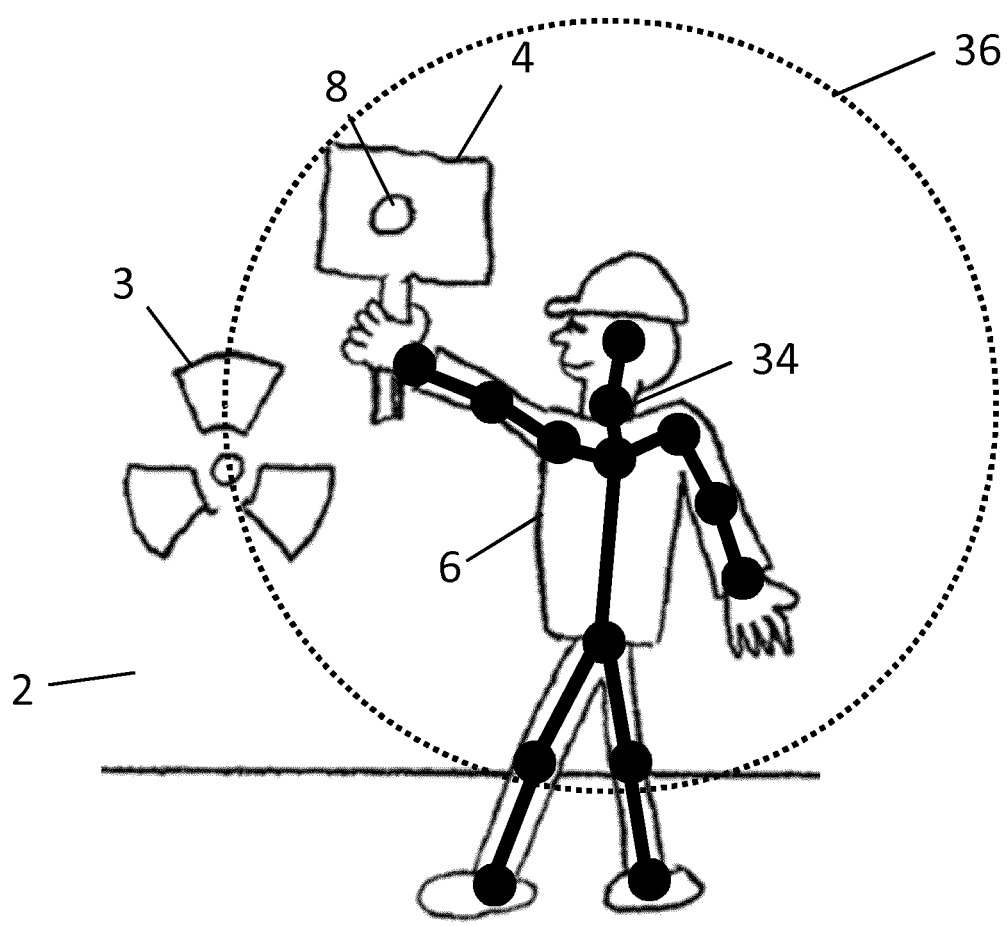
FIG. 4 shows the step of skeletal tracking processing according to an embodiment of the present invention.

FIG. 4 shows a user 6 performing a radiation survey of a surface 2 using a handheld radiation probe 4. The skeletal tracking processing performed by the processor 30 of the computer 16 (executing the skeletal tracking software) identifies the main joints and limbs of the user 6 performing the survey. This skeletal tracking is used to identify the position of the neck 34 of the user 6.

The processor 30 then searches a frame of video image data within a radius of 1.5 m from the neck 34 of the user 6 (i.e. within the circle 36 shown in FIG. 4) for the coloured patch 8 on the housing of the handheld radiation probe 4. Once identified, this enables the position of the handheld radiation probe 4 to be determined from the frame of video image data and the distance data, for each frame of video data captured (step 105, FIG. 3). For subsequent frames of video image data being processed, the starting point for searching for the coloured patch 8 on the housing of the handheld radiation probe 4 is the location of the coloured patch 8 in the immediately previous frame of video image data.

If the coloured patch 8 cannot be identified in a particular frame of video image data, the area being searched (e.g. based on the neck 34 of the user 6 or the previous position of the coloured patch 8 in the immediately previous frame of video image data) by the processor 30 is increased. If the coloured patch 8 still cannot be identified, the processor 30 signals to the handheld radiation probe 4 (via the transmitter 32 of the computer 16, the receiver 23 of the handheld radiation probe 4 and the alert output 21 of the handheld radiation probe 4) to cause the alert output 21 to output an audio, visual or haptic signal (as appropriate) to alert the user that the coloured patch 8 of the handheld radiation probe 4 appears not to be visible to the skeletal tracking device 10 (step 106, FIG. 3). The user 6 can then move the handheld radiation probe 4 so that the coloured patch 8 of the handheld radiation probe 4 appears visible to the skeletal tracking device 10, so that the survey may continue.

Once the position of the handheld radiation probe 4 has been identified by the processor 30 in a frame of video image data, its position relative to the surface 2 that it is being used to survey can be determined by the processor 30 using the distance data collected during the calibration of the system (step 107, FIG. 3). This relative position (i.e. the distance between the surface 2 and the handheld radiation probe 4) is then compared against the threshold distance, which is set as a parameter in the system. The processor 30 then determines if the relative position calculated is within the threshold distance (step 108, FIG. 3).

When the relative position is less than the threshold distance, the acquired data for that frame of video image data (i.e. the radiation concentration measurement and the associated position data, which are matched together using their associated time stamps) are flagged as being a valid measurement. When the relative position is greater than the threshold distance, the acquired data for that frame of video image data (i.e. the radiation concentration measurement and the associated position data, which are matched together using their associated time stamps) are flagged as being an invalid measurement. These data and the relevant associated flag are transmitted from the computer 16 via the transmitter 32 (for storage and/or further processing) and/or are written to the data recorder 34 (for storage, e.g. ahead of further processing) (step 109, FIG. 3).

In addition, the data are displayed on the display screen 18 of the computer, indicating the position, concentration and validity of the measurement (step 110, FIG. 3), e.g. using appropriate colouring. This allows the user 6 to obtain feedback of the survey as they are using the handheld radiation probe 4.

When an invalid measurement has been made, the processor 30 signals to the handheld radiation probe 4 (via the transmitter 32 of the computer 16, the receiver 23 of the handheld radiation probe 4 and the alert output 21 of the handheld radiation probe 4) to cause the alert output 21 to output an audio, visual or haptic signal (as appropriate and, e.g., differently to the alert for the coloured patch 8 not being visible) to alert the user that the handheld radiation probe 4 is not being held close enough to the surface 2 being surveyed to allow valid measurements to be taken of the potential radiation (step 111, FIG. 3). The user 6 can then move the handheld radiation probe 4 closer to the surface 2, so to take valid measurements. The user 6 can also see from the display on the display screen 18 which areas of the surface 2 need to be surveyed again to collect valid data.

As well as aiding the user 6 during the survey, the display produced (of the positions and associated concentrations of the radiation detected using the radiation monitor 19) can then be used to aid the removal of the radioactive material 3 from the enclosed environment 1.

Figure 5:
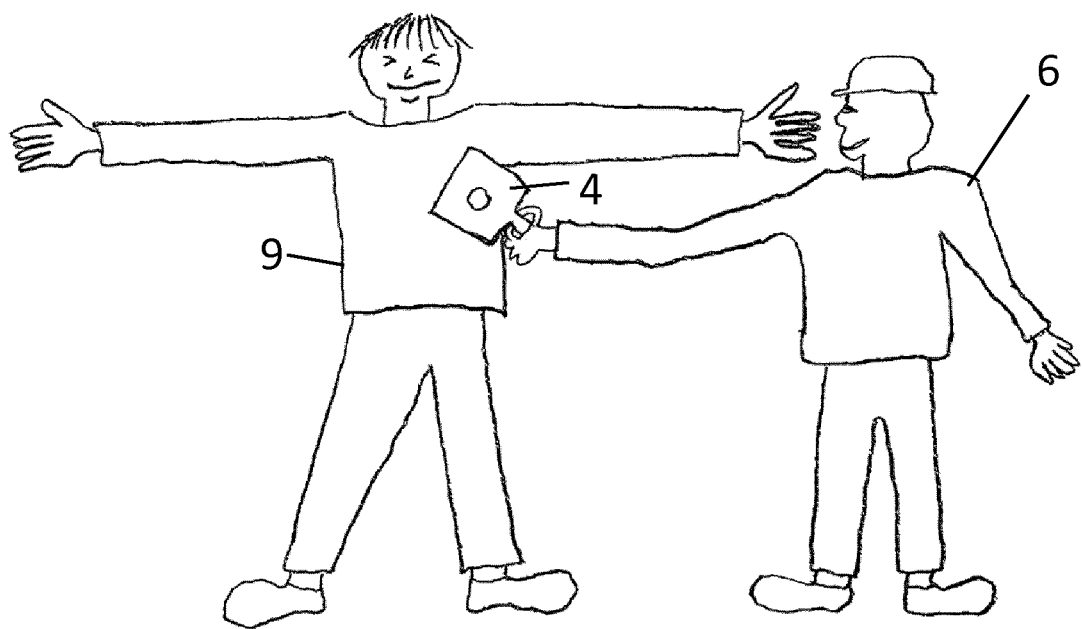
FIG. 5 shows the use of the system shown in FIGS. 1 and 2 according to another embodiment of the present invention.

The use of the system shown in FIGS. 1 and 2, according to another embodiment of the present invention will now be described, with reference to FIG. 5. FIG. 5 shows the system being used to perform a "frisking" survey of a worker 9 who has recently exited an environment (e.g. the enclosed environment shown in FIG. 1) in which they may have been exposed to radioactive material. Such a frisking survey either confirms that the worker has not been exposed to any radioactive material or identifies the location of any radioactive material so that it can be removed appropriately, e.g. by cleaning or disposal of the contaminated material.

The system used in this embodiment includes all of the components shown in FIGS. 1 and 2. However, for the purposes of clarity only the handheld radiation probe 4 is shown being used by a user 6 performing the survey.

Operation of the survey according to this embodiment of the invention proceeds in the manner described above and shown in FIG. 3, with two main exceptions.

First, the calibration of the system (step 101, FIG. 3) does not include a survey of a surface to be surveyed without the user present. Instead, the user 6 just surveys the surface of the worker 9 to be frisked (i.e. their skin, hair and clothing) (step 102, FIG. 3).

The second difference is that using the video image and depth sensing data collected during the survey, skeletal tracking of both the user 6 and the worker 9 is performed by the processor 30 (step 104, FIG. 3). This identifies both the position of the handheld radiation probe 4 (steps 105, 107, FIG. 3) and the positions of the surface of the worker 9 being surveyed. The acquired data can then be processed in the same way as the embodiment described above, with the surface of the worker 9 being considered in the same way as the surface 2 of the enclosed environment 1.

The result of such a frisking survey is that the location, concentration and validity of any radioactivity measurements can be determined and output.

It will be seen from the above that, at least in preferred embodiments, the present invention provides a system and method for surveying a surface for the presence of a contaminant. Skeletal tracking of the user performing the survey is used to determine the positions of any contaminant that is detected. This allows a detailed survey to be built up of the location and concentration of the contaminant, in an environment in which it may not be possible to use conventional location (e.g. GNSS) data. The contaminant can thus be identified which then allows it to be disposed of correctly.

It will be appreciated by those skilled in the art that only a small number of possible embodiments have been described and that many variations and modifications are possible within the scope of the invention. For example the system could be arranged to detect contaminants other than radioactive material. In this instance the radiation monitor would be substituted with a device to detect the presence of the contaminant to be surveyed.

The invention claimed is:

1. A system for surveying a surface to measure a physical or chemical property associated with the surface, the system comprising:
    a handheld probe, arranged to be held by a human user for measuring the physical or chemical property at a plurality of locations over the surface to be surveyed;
    a video camera for capturing a sequence of frames of video data of the surface and the handheld probe while the human user is using the handheld probe to survey the surface;

a depth sensing device for capturing depth sensing data of the surface and the handheld probe while the human user is using the handheld probe to survey the surface, wherein the depth sensing device is arranged to use the captured depth sensing data to measure a distance from the depth sensing device to the handheld probe being used to survey the surface;

processing circuitry configured to:
identify presence of the handheld probe in the sequence of frames of video data;
use the identification of the presence of the handheld probe and the measured distance from the depth sensing device to the handheld probe to determine a position of the handheld probe relative to the surface being surveyed by the handheld probe; and
compare the determined position of the handheld probe relative to the surface being surveyed by the handheld probe with a threshold distance from the surface being surveyed; and a data recorder and/or a data transmitter for recording and/or transmitting data representative of the physical or chemical property measured by the handheld probe and data representative of an associated position of the handheld probe, when the handheld probe is determined to be less than the threshold distance from the surface being surveyed;

wherein the video camera is positioned remote from the surface and the handheld probe such that in use the video camera is arranged to capture the sequence of frames of video data of the surface and the handheld probe while the human user using the handheld probe to survey the surface; and wherein the depth sensing device is positioned remote from the surface and the handheld probe such that in use the depth sensing device is arranged to capture the depth sensing data of the surface and the handheld probe while the human user is using the handheld probe to survey the surface.

2. The system as claimed in claim 1, herein the handheld probe comprises a handheld contaminant probe for detecting a concentration of a contaminant at the plurality of locations over the surface to be surveyed.

3. The system as claimed in claim 1, wherein the handhold probe comprises a handheld radiation monitor for detecting a concentration of radioactive material at the plurality of locations over the surface to be surveyed.

4. The system as claimed in claim 1, wherein the surface to be surveyed comprises a surface of a structural component in an enclosed environing, or a surface of a person in or having been in a potentially contaminated environment.

5. The system as claimed in claim 1, wherein the system comprises an integrated device comprising the video camera and the depth sensing device.

6. The system as claimed in claim 1, wherein the handheld probe, the video camera and the depth sensing device are arranged to generate and provide separate respective data streams to the processing circuitry.

7. The system as claimed in claim 1, wherein the data recorded and/or transmitted when the handheld probe is determined to be less than the threshold distance rom the surface being surveyed is identified as having been captured when the handheld probe was determined to be less than the threshold distance from the surface being surveyed.

8. The system as claimed in claim 1, wherein the handheld probe, the video camera and/or the depth sensing device are arranged to record data representative or a time at which their respective data are acquired.

9. The system as claimed in claim 1, wherein the processing circuitry is configured to determine the position of the handheld probe visually using the sequence of frames of video data.

10. The system as claimed in claim 9, wherein the handheld probe comprise a particular marking and the processing circuitry is configured to identify the particular marking using the frames of video data to determine the position of the handheld probe.

11. The system as claimed in claim 1, wherein the depth sensor is arranged to measure a distance from the device to the human user while the human user is using the handheld probe to survey the surface, and wherein the processing circuitry is configured to perform skeletal tracking of the human user using the sequence of frames of video image data and the determined distance to the human user to identify the handheld probe and to determine the position of the handheld probe relative to the surface being surveyed by the handheld probe.

12. The system as claimed in claim 11, wherein the processing circuitry is configured to determine the position of the handheld probe by determining the position of a particular part of a body of the human user using the skeletal tracking, and then looking in a vicinity of the determined particular part of the human user's body for the handheld probe.

13. The system as claimed in claim 11, wherein the processing circuitry is configured to perform the skeletal tracking in real time while the human user is performing the survey of the surface using the handheld probe.

14. The system as claimed in claim 1, wherein the processing circuitry is configured to determine the position of the handheld probe by looking in one frame of the sequence of frames of video data for the handheld probe in a vicinity of the location of the handheld probe in a previous frame of the sequence of frames of video data.

15. The system as claimed in claim 1, wherein the threshold distance is less than 20 cm.

16. The system as claimed in claim 1, wherein the system comprises a feedback device arranged to provide feedback information to the human user when the handheld probe is determined to be more than a threshold distance from the surface being surveyed, when the handheld probe cannot be identified using the frames of video image data and/or when the handheld probe is being moved too quickly over the surface being surveyed.

17. The system as claimed in claim 1, wherein the system comprises a display screen arranged to display points on the surface that have been surveyed by the handheld probe, the physical or chemical property measured by the handheld probe at each of the points on the surface that have been surveyed and/or the points on the surface that have been surveyed by the handheld probe when the handheld probe was within the threshold distance from the points on the surface being surveyed.

18. The system as claimed in claim 1, wherein the surface to be surveyed comprises the surface of a person that has been in a potentially contaminated environment, wherein the depth sensing device is arranged to determine the distance from the device both to the human user performing the survey and the person being surveyed, and wherein the processing circuitry is configured to perform skeletal tracking of the human user performing the survey and the person being surveyed using the sequence of frames of video data and the determined distances to the human, user and to the person being surveyed to determine the position of the handheld probe relative to the surface being surveyed by the handheld probe.

19. A method of surveying a surface to measure a physical or chemical associated with the surface, the method comprising: measuring the physical or chemical property at a plurality of locations over the surface to be surveyed using a handheld probe held by a human user: capturing a sequence of frames of video data, using a video camera, of the handheld probe while the human user is using the handheld probe to survey the surface; capturing depth sensing data of the surface and the handheld probe while the human user is using the handheld probe to survey the surface, the depth sensing device using the captured depth sensing data to measure a distance from the depth sensing device to the handheld probe being used to survey the surface; identifying presence of the handheld probe in the sequence of frames of video data; using the identification of the presence of the handheld probe and the measured distance to the handheld probe to determine a position of the handheld probe relative to the surface being surveyed by the handheld probe; comparing the determined position of the handheld probe relative to the surface being surveyed by the handheld probe with a threshold distance from the surface being surveyed; and recording and/or transmitting data representative of the physical or chemical property measured by the handheld probe and data representative of an associated position of the handheld probe, when the handheld probe is determined to be less than the threshold distance from the surface being surveyed; wherein the video camera is positioned remote from the surface and the handheld probe such that in use the video camera is arranged to capture the sequence of frames of video data of the surface and the handheld probe while the human user using the handheld probe to survey the surface; and wherein the depth sensing device is positioned remote from the surface and the handheld probe such that in use the depth sensing device is arranged to capture the depth sensing data of the surface and the handheld probe while the human user is using the handheld probe to survey the surface.

* * * * *